United States Patent
Peddy et al.

(10) Patent No.: US 11,292,793 B2
(45) Date of Patent: Apr. 5, 2022

(54) SOLID DISPERSIONS OF AMORPHOUS LUMATEPERONE P-TOSYLATE

(71) Applicant: DR. REDDY'S LABORATORIES LIMITED, Hyderabad (IN)

(72) Inventors: Vishweshwar Peddy, Hyderabad (IN); Raja Sekhar Voguri, Hyderabad (IN)

(73) Assignee: DR. REDDY'S LABORATORIES LIMITED, Hyderabad (IN)

(*) Notice: Subject to any disclaimer, the term of this patent is extended or adjusted under 35 U.S.C. 154(b) by 36 days.

(21) Appl. No.: 16/603,418

(22) PCT Filed: Apr. 9, 2018

(86) PCT No.: PCT/IB2018/052453
§ 371 (c)(1),
(2) Date: Oct. 7, 2019

(87) PCT Pub. No.: WO2018/189646
PCT Pub. Date: Oct. 18, 2018

(65) Prior Publication Data
US 2020/0148683 A1    May 14, 2020

(30) Foreign Application Priority Data

Apr. 10, 2017 (IN) .............................. 201741012769

(51) Int. Cl.
| A61K 31/4985 | (2006.01) |
| C07D 487/22 | (2006.01) |
| C07D 471/16 | (2006.01) |
| A61K 9/10 | (2006.01) |
| A61K 9/16 | (2006.01) |
| A61K 47/38 | (2006.01) |

(52) U.S. Cl.
CPC .............. *C07D 471/16* (2013.01); *A61K 9/10* (2013.01); *A61K 9/16* (2013.01); *A61K 47/38* (2013.01); *C07B 2200/13* (2013.01)

(58) Field of Classification Search
CPC .......................... A61K 31/4985; C07D 487/22
USPC .......................................... 514/250; 544/343
See application file for complete search history.

(56) References Cited

U.S. PATENT DOCUMENTS

| 8,648,077 B2 | 2/2014 | Tomesch et al. |
| 2016/0030425 A1 | 2/2016 | Mates et al. |
| 2019/0192511 A1* | 6/2019 | Li ................. A61K 31/4985 |

FOREIGN PATENT DOCUMENTS

| WO | 2000077002 A1 | 12/2000 |
| WO | 2008112280 A1 | 9/2008 |
| WO | 2009114181 A2 | 9/2009 |
| WO | 2009145900 A1 | 12/2009 |
| WO | 2013155504 A1 | 10/2013 |
| WO | 2017172784 A1 | 10/2017 |
| WO | 2017172811 A1 | 10/2017 |
| WO | 2018031535 A1 | 2/2018 |

OTHER PUBLICATIONS

Swati Sareen et al, Improvement in solubility of poor water-soluble drugs by solid dispersion, Int. J. Pharm. Investig. Jan.-Mar. 2012; 2(1): 12-17.
Li P et al. Discovery of a Tetracyclic Quinoxaline Derivative as a Potent and Orally Active Multifunctional Drug Candidate for the Treatment of Neuropsychiatric and Neurological Disorders, J. Med. Chem., (Feb. 21, 2014), vol. 57 pp. 2670-2682 (Abstract).
International Search Report dated Dec. 9, 2018, for corresponding International Patent Application No. PCT/IB2018/052453.
Written Opinion dated Dec. 9, 2018, for corresponding International Patent Application No. PCT/IB2018/052453.

* cited by examiner

*Primary Examiner* — Douglas M Willis
(74) *Attorney, Agent, or Firm* — Pergament & Cepeda LLP; Milagros A. Cepeda; Edward D. Pergament (57) ABSTRACT

The present application relates to solid state forms of Lumateperone p-Tosylate and processes for preparation thereof. The present application provides amorphous Lumateperone p-tosylate and a solid dispersion comprising amorphous Lumateperone p-tosylate and one or more pharmaceutically acceptable polymers and processes for preparation thereof. The compounds are useful as 5-HT$_2$ receptor agonists and antagonists used in treating disorders of the central nervous system including a disorder associated with 5HT$_{2C}$ or 5HT$_{2A}$ receptor modulation.

2 Claims, 3 Drawing Sheets

SOLID DISPERSIONS OF AMORPHOUS LUMATEPERONE P-TOSYLATE

This application is a National Stage Application under 35 U.S.C. § 371 of PCT International Application No. PCT/IB2018/052453, filed Apr. 9, 2018, which takes priority from Indian Provisional Application Number IN 201741012769, filed Apr. 10, 2017, all of which are herein incorporated by reference in their entirety.

FIELD OF THE APPLICATION

The present application relates to solid state forms of Lumateperone p-Tosylate and processes for preparation thereof.

The drug compound is having the adopted name "Lumateperone" and it has chemical name: 1-(4-fluorophenyl)-4-[(6bR,10aS)-2,3,6b,9,10,10a-hexahydro-3-methyl-1H-pyrido[3',4':4,5]pyrrolo[1,2,3-de]quinoxalin-8(7H)-yl] 1-Butanone; and a structure depicted by Formula I.

Formula I

International Patent Application Publication Nos. WO2000077002A1, WO2009145900A1 and WO2013155504A1 which are incorporated herein in their entirety reported Lumateperone and its related compounds. These compounds have been found to be useful as 5-HT2 receptor agonists and antagonists used in treating disorders of the central nervous system including a disorder associated with 5HT2C or 5HT2A receptor modulation selected from obesity, anorexia, bulimia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, gastrointestinal disorders such as dysfunction of the gastrointestinal tract motility. International Patent Application Publication No. WO2008112280A1 disclose process(es) for preparing Lumateperone and its salts.

International Patent Application Publication No. WO2009114181A2 disclose crystalline forms of the p-Tosylate salt of compound of Formula (I), WO 2017172784 A1 disclose oxalate, aminosalicylate, cyclamate salts of Lumateperone, WO 2017172811 A1 disclose co-crystal of Lumateperone with iso-nicotinamide, nicotinatinamide, WO 2018031535 A1 disclose crystalline Form F1 of Lumateperone ditosylate.

Crystalline solids normally require a significant amount of energy for dissolution due to their highly organized, lattice like structures. For example, the energy required for a drug molecule to escape from a crystal is more than from an amorphous or a non-crystalline form. It is known that the amorphous forms in a number of drugs exhibit different dissolution characteristics and in some cases different bioavailability patterns compared to the crystalline form. For some therapeutic indications, one bioavailability pattern may be favored over another. Therefore, it is desirable to have amorphous forms of drugs with high purity to meet the needs of regulatory agencies and also highly reproducible processes for their preparation.

In view of the above, it is therefore, desirable to stable amorphous form of Lumateperone p-tosylate. The amorphous form provided herein is at least stable under ordinary stability conditions with respect to purity, storage and is free flowing powder.

Amorphous solid dispersions of drugs are generally known to improve the stability and solubility of drug products. However, some of such amorphous solid dispersions are found to be unstable over time. Amorphous solid dispersions of drugs tend to convert to crystalline forms over time, which can lead to improper dosing due to differences of the solubility of crystalline drug material compared to amorphous drug material. The present invention, however provides stable amorphous solid dispersions of Lumateperone p-tosylate with improved solubility. Moreover, the present invention provides solid dispersions of Lumateperone p-tosylate which may be reproduced easily and is amenable for processing into a dosage form.

SUMMARY OF THE INVENTION

In the first embodiment, the present application provides Lumateperone p-tosylate in amorphous form.

Figure 1:
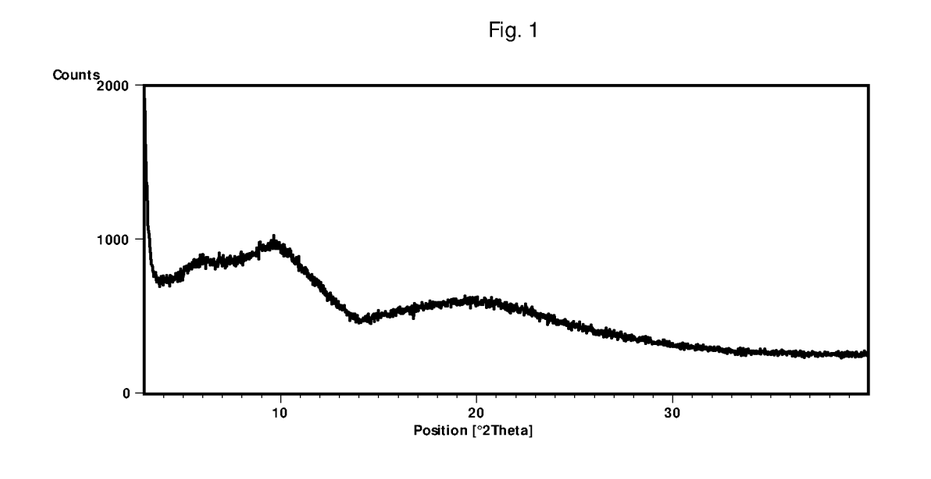
FIG. 1 is an illustration of powder X-ray diffraction ("PXRD") pattern of Lumateperonep-tosylate amorphous form prepared according to example 1.
Figure 2:
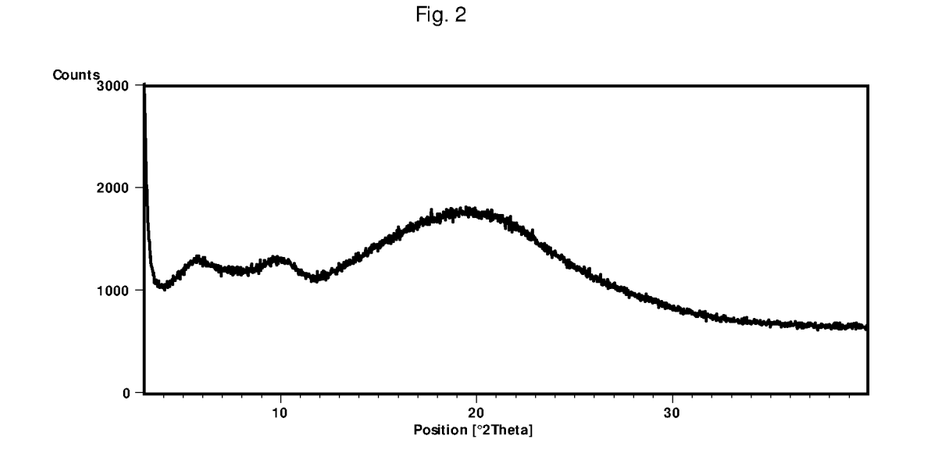
FIG. 2 is an illustration of powder X-ray diffraction ("PXRD") pattern of Lumateperone p-tosylate amorphous form prepared according to example 3.

In the second embodiment, the present application provides amorphous Lumateperone p-tosylate that can be characterized by its PXRD pattern as illustrated by FIG. 1 or FIG. 2.

In the third embodiment, the present application provides processes for preparing an amorphous form of Lumateperonep-tosylate, comprising the steps of:
a) providing a solution of Lumateperone p-tosylate in a solvent; and
b) isolating amorphous Lumateperone p-tosylate.

In the fourth embodiment, the present application provides a pharmaceutical composition comprising an amorphous form of Lumateperone p-tosylate and one or more pharmaceutically acceptable excipients.

In the fifth embodiment, the present application provides a solid dispersion comprising amorphous Lumateperone p-tosylate and one or more pharmaceutically acceptable polymers.

In the sixth embodiment, the present application provides a method for preparing a solid dispersion comprising amorphous Lumateperone p-tosylate and one or more pharmaceutically acceptable polymers comprising the steps of:
a) providing a mixture of Lumateperone p-tosylate and one or more pharmaceutically acceptable polymers in a solvent; and
b) isolating solid dispersion comprising amorphous Lumateperone p-tosylate and one or more pharmaceutically acceptable polymers.

DESCRIPTION OF THE INVENTION

In an embodiment, the present application provides processes for preparing an amorphous form of Lumateperonep-tosylate, comprising the steps of:
a) providing a solution of Lumateperone p-tosylate in a solvent; and
b) isolating amorphous Lumateperone p-tosylate.
Providing a solution in step a) includes:
i) direct use of a mixture containing Lumateperone p-tosylate that is either obtained in the course of its synthesis or prepared by dissolving Lumateperone p-tosylate in a suitable solvent; or
ii) treating Lumateperone free form with p-toluenesulfonic acid in a suitable solvent.

Any physical form of Lumateperone p-tosylate may be utilized in step (a) of the process embodiments herein above.

Suitable solvents which can be used in step (a) for the preparation of amorphous Lumateperone p-tosylate can be chosen by person skilled in the art from the below list of solvents that include but are not limited to: alcoholic solvents such as methanol, ethanol, isopropyl alcohol, n-propanol, isoamyl alcohol and the like; ketones such as acetone, ethyl methyl ketone, methyl isobutyl ketone and the like; esters such as ethyl acetate, n-propyl acetate, n-butyl acetate, t-butyl acetate and the like; ethers such as diethyl ether, dimethyl ether, di-isopropyl ether, 1,4-dioxane and the like; nitriles such as acetonitrile, propionitrile and the like; halogenated hydrocarbons such as dichloromethane, 1,2-dichloroethane, chloroform, carbon tetrachloride and the like; hydrocarbons such as toluene, xylene and the like; organic acids such as formic acid, acetic acid and the like; solvents like DMSO, DMF, DMA and the like; water and any mixtures of two or more thereof.

The solution obtained in step (a) may be optionally filtered to remove any insoluble particles. Suitable techniques to remove insoluble particles are filtration, micron filter, centrifugation, decantation, and any other techniques known in the art. The solution can be filtered by passing through paper, glass fiber, or other membrane material, or a clarifying agent such as celite. Depending upon the equipment used and the concentration and temperature of the solution, the filtration apparatus may need to be preheated to avoid premature precipitation of solid.

Step (b) involves isolating the amorphous Lumateperonep-tosylate.

In one aspect present application involves isolation of amorphous Lumateperone p-tosylate by removing solvent from a solution obtained in step (a) or by addition of suitable anti-solvent in a solution obtained in step (a) or by cooling to appropriate temperature resulting in formation of amorphous form. Suitable techniques which can be used for the removal of solvent include but not limited to evaporation, flash evaporation, simple evaporation, rotational drying, spray drying, thin-film drying (e.g., agitated thin-film drying (ATFD)), agitated nutsche filter drying, pressure nutsche filter drying, freeze-drying, rotary vacuum paddle dryer (RVPD) or any other suitable technique known in the art.

The solvent can be removed, optionally under reduced pressures, at temperatures less than about 100° C., less than about 75° C., less than about 60° C., less than about 50° C., less than about 40° C. or any other suitable temperatures.

Suitable anti-solvent that can be employed can be chosen by the person skilled in the art from the aforementioned list of solvents.

Suitable temperature at which the mixture of step a) can be cooled include but not limited to any temperature less than 60° C., preferably less than 40° C., more preferably less than 20° C.

In another aspect present application involves recovery of an amorphous form of Lumateperone p-tosylate after removal of solvent. The said recovery can be done by using the processes known in the art. The resulting solid may be collected by using techniques such as by scraping, or by shaking the container, or other techniques specific to the equipment used.

The resulting compound may be optionally further dried to afford an amorphous form of Lumateperone p-tosylate. Drying can be carried out in a tray dryer, vacuum oven, air oven, cone vacuum dryer, rotary vacuum dryer, fluidized bed dryer, spin flash dryer, flash dryer, or the like. The drying can be carried out at temperatures of less than about 100° C., less than about 70° C., less than about 40° C., less than about 30° C., less than about 20° C., or any other suitable temperatures; at atmospheric pressure or under a reduced pressure; as long as the Lumateperone p-tosylate is not degraded in its quality. The drying can be carried out for any desired times until the required product quality is achieved. Suitable time for drying can vary from few minutes to several hours for example from about 30 minutes to about 24 or more hours.

In yet another embodiment amorphous form can be prepared by melting of Lumateperone p-tosylate by techniques known in the art like Hot Melt Extrusion (HME), Twin Screw Extrusion (TSE)

In another embodiment, the present application provides amorphous form of Lumateperonep-tosylate (1:1) as characterized by FIGS. 1 and 2.

In yet another embodiment, the present application provides a solid dispersion comprising amorphous Lumateperone p-tosylate and one or more pharmaceutically acceptable polymers.

Solid dispersion as used herein refers to the dispersion of one or more active ingredients in an inert excipient or polymer or carrier, where the active ingredients could exist in finely crystalline, solubilized or amorphous state (Sareen et al., 2012 and Kapoor et al., 2012). Solid dispersion consists of two or more components, generally a polymer or carrier and drug optionally along with stabilizing agent (and/or surfactant or other additives). The most important role of the added polymer in solid dispersion is to reduce the molecular mobility of the drug to avoid the phase separation and re-crystallization of drug during storage. The resulting solid dispersions may have increased solubility. The increase in solubility of the drug in solid dispersion is mainly because drug remains in amorphous form which is associated with a higher energy state as compared to crystalline counterpart and due to that it requires very less external energy to dissolve.

A solid dispersion is a molecular dispersion of a compound, particularly a drug substance within a polymer or carrier. Formation of a molecular dispersion provides a means of reducing the particle size to nearly molecular levels (i.e. there are no particles). As the polymer dissolves, the drug is exposed to the dissolution media as fine particles that are amorphous, which can dissolve and be absorbed more rapidly than larger particles.

In general, the term "solid dispersion" refers to a system in a solid state comprising at least two components, wherein one component is dispersed throughout the other component or components. The term "solid dispersion" as used herein, refers to stable solid dispersions comprising amorphous drug substance and one or more polymers or carriers. Further the term "solid dispersion" as used herein also refers to stable solid dispersions comprising amorphous drug substance and one or more polymers or carriers with or without adsorbent/absorbent. By "amorphous drug substance," it is meant that the amorphous solid contains drug substance in a substantially amorphous solid state form i.e. at least about 80% of the drug substance in the dispersion is in an amorphous form. More preferably at least about 90% and most preferably at least about 95% of the drug substance in the dispersion is in amorphous form.

The solid dispersions of Lumateperone p-tosylate of the present invention can be made by any of numerous methods that result in a solid dispersion comprising an amorphous Lumateperone p-tosylate. Several approaches can be used for the preparation of solid dispersion which includes spray drying, fusion method, solvent evaporation, hot-melt extrusion, particle size reduction, supercritical fluid (SCF) processes, kneading, inclusion complexes, electrostatic spinning method, melt crystallization and surface-active carriers.

Lumateperonep-tosylate can be incorporated in the dispersion in amorphous form.

The dispersing agent is typically composed of a pharmaceutically acceptable substance that does not substantially interfere with the pharmaceutical action of Lumateperone p-tosylate. The phrase "pharmaceutically acceptable" is employed herein to refer to those substances which are, within the scope of sound medical judgment, suitable for use in contact with the tissues of human beings and animals without excessive toxicity, irritation, allergic response, or other problem or complication, commensurate with a reasonable benefit/risk ratio. In some embodiments, the carrier is a solid at room temperature (e.g., about 22° C.).

Non-limiting examples of suitable polymers or carriers such as celluloses (e.g., carboxymethylcelluloses, methylcelluloses, hydroxypropylcelluloses, hydroxypropylmethylcelluloses); polysaccharides, heteropolysaccharides (pectins); poloxamers; poloxamines; ethylene vinyl acetates; polyethylene glycols; dextrans; polyvinylpyrrolidones; chitosans; polyvinylalcohols; propylene glycols; polyvinylacetates; phosphatidylcholines (lecithins); miglyols; polylactic acid; polyhydroxybutyric acid; mixtures of two or more thereof, copolymers thereof, derivatives thereof, and the like. Further examples of carriers include copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of N-vinyl purine (or pyrimidine) derivatives and N-vinylpyrrolidone.

An enteric coating polymer can also be used according to the present invention. Specific examples of the enteric coating polymers include cellulose acetate phthalate, cellulose acetate trimellitate, cellulose acetate succinate, hydroxymethylcellulose ethyl phthalate, hydroxypropylmethylcellulose phthalate, eudragit, hydroxypropylmethylcellulose acetate succinate, hydroxypropylmethyl acetate maleate, hydroxypropylmethyl trimellitate, carboxymethylethylcellulose, polyvinyl butyrate phthalate, polyvinyl alcohol acetate phthalate, methacrylic acid/ethyl acrylate copolymer, and methacrylic acid/methyl methacrylate copolymer, hydroxypropyl methylcellulose phthalate, hydroxypropylmethylcellulose acetate succinate, hydroxypropylmethyl acetate maleate and hydroxypropylmethyl trimellitate.

In an aspect of the invention, the polymer is polyvinylpyrrolidone (PVP) or a derivative thereof. PVP is a polyamide that forms complexes with a wide variety of substances and is considered to be chemically and physiologically inert. Examples of suitable PVPs include polyvinylpyrrolidones having an average molecular weight from about 10,000 to about 50,000. In some embodiments, the polyvinylpyrrolidone has an average molecular weight of about 10,000 to about 20,000. In further embodiments, the polyvinylpyrrolidone has a molecular weight of about 15,000 to about 20,000.

In another embodiment, the present application provides a method for preparing a solid dispersion comprising amorphous Lumateperone p-tosylate and one or more pharmaceutically acceptable polymers comprising the steps of:

a) providing a mixture of Lumateperone p-tosylate and one or more pharmaceutically acceptable polymers in a solvent; and b) isolating solid dispersion comprising amorphous Lumateperone p-tosylate and one or more pharmaceutically acceptable polymers.

Any physical form of Lumateperone p-tosylate may be utilized for providing the mixture of Lumateperone p-tosylate in step (a).

In an aspect for the preparation of solid dispersion comprising amorphous Lumateperonep-tosylate and one or more pharmaceutically acceptable polymers or carriers, step (a) involves mixing Lumateperone p-tosylate and one or more pharmaceutically acceptable polymers or carriers for providing a solution or a suspension in step (a).

Any undissolved particles in the solution obtained in step (a) may be removed by suitable method as described herein above or any other technique known in the art.

In cases where mixture of step a) is a suspension, the solution of Lumateperone p-tosylate in a solvent can be filtered prior to addition of one or more pharmaceutically acceptable polymers or carriers.

Suitable solvent which can be used for preparing the solid dispersion of Lumateperonep-tosylate are the same as described herein above.

Suitable pharmaceutically acceptable polymers or carriers that are dispersing agents which can be used in step (a) include, but are not limited to: diluents such as starches, pregelatinized starches, lactose, powdered celluloses, microcrystalline celluloses, dicalcium phosphate, tricalcium phosphate, mannitol, sorbitol, sugar and the like; binders such as acacia, guar gum, tragacanth, gelatin, polyvinylpyrrolidones, hydroxypropyl celluloses, hydroxypropyl methylcelluloses, pregelatinized starches and the like; disintegrants such as starches, sodium starch glycolate, pregelatinized starches, crospovidones, croscarmellose sodium, colloidal silicon dioxide and the like; lubricants such as stearic acid, magnesium stearate, zinc stearate and the like; glidants such as colloidal silicon dioxide (Syloid, Aerosil, Cab-o-sil etc.) and the like; solubility or wetting enhancers such as anionic or cationic or neutral surfactants; complex forming agents such as various grades of cyclodextrins and resins; release rate controlling agents such as hydroxypropyl celluloses, hydroxymethyl celluloses, hydroxypropyl methylcelluloses, ethylcelluloses, methylcelluloses, various grades of methyl methacrylates, waxes and the like. Other pharmaceutically acceptable excipients that are of use include but are not limited to: film formers, plasticizers, colorants, flavoring agents, sweeteners, viscosity enhancers, preservatives, antioxidants, and the like.

The step (b) involves isolation of solid dispersion comprising amorphous Lumateperonep-tosylate and one or more pharmaceutically acceptable polymers.

In one aspect, isolation of solid dispersion can be carried out by removing solvent from a solution obtained in step (a).

Suitable techniques which can be used for the removal of solvent are the same as described herein above or any other technique known in the art.

Although the solid dispersions of the present invention are preferably prepared using conventional spray drying techniques, it will be understood that suitable solid dispersions may be formed utilizing other conventional techniques known to those skilled in the art, such as vacuum drying, ATFD, fluid-bed drying, freeze-drying, rotary evaporation, drum drying, or other solvent removal process.

Another aspect of the invention involves preparation of solid dispersions of Lumateperonep-tosylate by melt processing, wherein the compound and a carrier are heated to a temperature above the melting point of both the carrier and compound, which results in the formation of a fine colloidal (as opposed to molecular) dispersion of compound particles, with some solubilization of the compound in the carrier matrix. Processing of such a molten mixture often includes rapid cooling, which results in the formation of a congealed mass which must be subsequently milled to produce a powder which can be filled into capsules or made into tablets.

In another aspect present application involves recovery of solid dispersion comprising an amorphous form of Lumateperone p-tosylate and one or more pharmaceutically acceptable polymers or carriers. The said recovery can be carried out by methods as described herein above or any other technique known in the art.

The resulting solid dispersion comprising an amorphous form of Lumateperone p-tosylate and one or more pharmaceutically acceptable polymers or carriers may be optionally further dried. Drying can be can be carried out by methods as described herein above or any other technique known in the art.

The amount of Lumateperone p-tosylate in the solid dispersions of the present invention ranges from about 0.1% to about 90% by weight of the solid dispersion; or from about 10% to about 70% by weight of the solid dispersion; or from about 20% to about 60% by weight of the solid dispersion; or from about 20% to about 40% by weight of the solid dispersion; or about 30% by weight of the solid dispersion. In some aspects, the weight ratio of Lumateperone p-tosylate to polymer or carrier is about 1:99 to about 99:1. In some aspects, the weight ratio of Lumateperone p-tosylate to polymer or carrier is about 1:99 to about 75:25 or about 1:99 to about 60:40. In further aspects, the weight ratio of Lumateperone p-tosylate to polymer or carrier is about 1:99 to about 15:85; about 1:99 to about 10:90; or about 1:99 to about 5:95. In further aspects, the weight ratio of Lumateperone p-tosylate to polymer or carrier is about 25:75 to about 75:25, about 40:60 to about 60:40 or about 1:1 or about 2:1. Typically, Lumateperone p-tosylate and carrier medium are present in a ratio by weight with the solvent of 1:0.1 to 1:20.

Amorphous forms or the solid dispersions of Lumateperone p-tosylate of the present application can be optionally subjected to a particle size reduction procedures before or after the completion of drying of the product to produce desired particle sizes and distributions. Milling or micronization can be performed to achieve the desired particle sizes or distributions. Equipment that may be used for particle size reduction include, without limitation thereto, ball mills, roller mills, hammer mills, and jet mills.

In another general aspect, there is provided amorphous form of Lumateperone p-tosylate or solid dispersion comprising amorphous form of Lumateperone p-tosylate having particle size distributions wherein D90 is less than about 500 microns or less than about 200 microns or less than about 100 microns or less than about 50 microns or less than about 40 microns or less than about 30 microns or less than about 20 microns or less than about 10 microns or any other suitable particle sizes.

In an aspect, the present application provides pharmaceutical formulations comprising an amorphous form of Lumateperone p-tosylate or solid dispersion comprising amorphous form of Lumateperone p-tosylate, together with one or more pharmaceutically acceptable excipients. Lumateperone p-tosylate together with one or more pharmaceutically acceptable excipients of the present application may be formulated as: solid oral dosage forms such as, but not limited to, powders, granules, pellets, tablets, and capsules; liquid oral dosage forms such as, but not limited to, syrups, suspensions, dispersions, and emulsions; and injectable preparations such as, but not limited to, solutions, dispersions, and freeze dried compositions. Formulations may be in the forms of immediate release, delayed release, or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared using any one or more of techniques such as direct blending, dry granulation, wet granulation, and extrusion and spheronization. Compositions may be presented as uncoated, film coated, sugar coated, powder coated, enteric coated, and modified release coated.

Pharmaceutically acceptable excipients that are useful in the present application include, but are not limited to: diluents such as starches, pregelatinized starches, lactose, powdered celluloses, microcrystalline celluloses, dicalcium phosphate, tricalcium phosphate, mannitol, sorbitol, sugar, and the like; binders such as acacia, guar gum, tragacanth, gelatin, polyvinylpyrrolidones, hydroxypropyl celluloses, hydroxypropyl methyl celluloses, pregelatinized starches, and the like; disintegrants such as starches, sodium starch glycolate, pregelatinized starches, crospovidones, croscarmellose sodium, colloidal silicon dioxide, and the like; lubricants such as stearic acid, magnesium stearate, zinc stearate, and the like; glidants such as colloidal silicon dioxide and the like; solubility or wetting enhancers such as anionic, cationic, or neutral surfactants; complex forming agents such as various grades of cyclodextrins and resins; and release rate controlling agents such as hydroxypropyl celluloses, hydroxymethyl celluloses, hydroxypropyl methylcelluloses, ethylcelluloses, methylcelluloses, various grades of methyl methacrylates, waxes, and the like. Other pharmaceutically acceptable excipients that are useful include, but are not limited to, film formers, plasticizers, colorants, flavoring agents, sweeteners, viscosity enhancers, preservatives, antioxidants, and the like.

The pharmaceutical dosage form according to the present invention may be is coated with one or more coating materials or uncoated. The coating materials are not particularly limited and are known to the person skilled in the art.

The pharmaceutical dosage form according to the present invention can further comprise additional excipients and adjuvants, which are pharmaceutically acceptable and general coating materials, which are preferably applied as a coating to the pharmaceutical dosage form of the present invention. Such further excipients and adjuvants are known to the person skilled in the art.

The pharmaceutical compositions of the present invention are generally administered orally to patients, which include, but are not limited to, mammals, for example, humans, in the form of, for example, a hard or soft gelatin capsule, a tablet, a caplet, pills, granules or a suspension. The pharmaceutical dosage form can be prepared by methods known in the art, such as direct compression or wet granulation or direct compression. The compression of the blend to tablet cores can be carried out using a conventional tabletting machine or a rotary compression machine. The tablet cores may vary in shape and can be, for example, round, oval, oblong, cylindrical or any other suitable shape. The cores may also vary in size depending on the concentration of the therapeutic agent.

Lumateperone p-tosylate which may be used as the input in the process for preparation of the solid states of the present application can be prepared by any process known in the art.

The solid form of Lumateperone p-tosylate of the present application may be characterized by means of Powder X-ray Diffraction Pattern (PXRD). Other techniques, such as solid state NMR, Fourier Transform Infrared (FTIR), differential scanning calorimetry (DSC) may also be used.

The compound of this application is best characterized by the X-ray powder diffraction pattern determined in accordance with procedures that are known in the art. PXRD data reported herein was obtained using CuKα radiation, having the wavelength 1.5406 Å and were obtained using a Bruker AXS D8 Advance Powder X-ray Diffractometer and PANalytical X'Pert Pro instruments. For a discussion of these techniques see J. Haleblian, J. Pharm. Sci. 1975 64:1269-1288, and J. Haleblian and W. McCrone, J. Pharm. Sci. 1969 58:911-929.

Generally, a diffraction angle (2θ) in powder X-ray diffractometry may have an error in the range of ±0.2°. Therefore, the aforementioned diffraction angle values should be understood as including values in the range of about ±0.2°. Accordingly, the present application includes not only crystals whose peak diffraction angles in powder X-ray diffractometry completely coincide with each other, but also crystals whose peak diffraction angles coincide with each other with an error of about ±0.2°. Therefore, in the present specification, the phrase "having a diffraction peak at a diffraction angle (2θ±0.2°) of 7.9°" means "having a diffraction peak at a diffraction angle (2θ) of 7.7° to 8.1°". Although the intensities of peaks in the x-ray powder diffraction patterns of different batches of a compound may vary slightly, the peaks and the peak locations are characteristic for a specific polymorphic form. Alternatively, the term "about" means within an acceptable standard error of the mean, when considered by one of ordinary skill in the art. The relative intensities of the PXRD peaks can vary depending on the sample preparation technique, crystal size distribution, various filters used, the sample mounting procedure, and the particular instrument employed. Moreover, instrument variation and other factors can affect the 2-theta values. Therefore, the term "substantially" in the context of PXRD is meant to encompass that peak assignments can vary by plus or minus about 0.2 degree. Moreover, new peaks may be observed or existing peaks may disappear, depending on the type of the machine or the settings (for example, whether a Ni filter is used or not).

The D10, D50, and D90 values are useful ways for indicating a particle size distribution. D90 refers to at least 90 volume percent of the particles having a size smaller than the said value. Likewise, D10 refers to 10 volume percent of the particles having a size smaller than the said value. D50 refers to 50 volume percent of the particles having a size smaller than the said value. Methods for determining D10, D50, and D90 include laser diffraction, such as using equipment from Malvern Instruments Ltd. of Malvern, Worcestershire, United Kingdom.

Certain specific aspects and embodiments of the present application will be explained in greater detail with reference to the following examples, which are provided by way of illustration only and should not be construed as limiting the scope of the application in any manner.

Definitions

The following definitions are used in connection with the present application unless the context indicates otherwise. Polymorphs are different solids sharing the same molecular formula, yet having distinct physical properties when compared to other polymorphs of the same formula. The abbreviation "MC" mean moisture content. Moisture content can be conveniently measured, for example, by the Karl Fischer method.

"Amorphous form" as used herein refers to a solid state wherein the amorphous content with in the said solid state is at least about 35% or at least about 40% or at least about 45% or at least about 50% or at least about 55% or at least about 60% or at least about 65% or at least about 70% or at least about 75% or at least about 80% or at least about 85% or at least about 90% or at least about 95% or at least about 96% or at least about 97% or at least about 98% or at least about 99% or about 100%.

All percentages and ratios used herein are by weight of the total composition, unless the context indicates otherwise. All temperatures are in degrees Celsius unless specified otherwise and all measurements are made at 25° C. and normal pressure unless otherwise designated. The present disclosure can comprise the components discussed in the present disclosure as well as other ingredients or elements described herein.

As used herein, "comprising" means the elements recited, or their equivalents in structure or function, plus any other element or elements which are not recited. The terms "having" and "including" are also to be construed as open ended unless the context suggests otherwise.

All ranges recited herein include the endpoints, including those that recite a range "between" two values.

Terms such as "about," "generally," "substantially," or the like are to be construed as modifying a term or value such that it is not an absolute. Such terms will be defined by the circumstances and the terms that they modify, as those terms are understood by those of skill in the art. This includes, at very least, the degree of expected experimental error, technique error and instrument error for a given technique used to measure a value.

Where this document refers to a material, such as in this instance, Lumateperone p-tosylate, and their solid state forms thereof by reference to patterns, spectra or other graphical data, it may do so by qualifying that they are "substantially" shown or as depicted in a Figure, or by one or more data points. By "substantially" used in such a context, it will be appreciated that patterns, spectra and other graphical data can be shifted in their positions, relative intensities and/or values due to a number of factors known to those of skill in the art.

In addition, where a reference is made to a figure, it is permissible to, and this document includes and contemplates, the selection of any number of data points illustrated in the figure which uniquely define that solid state form, within any associated and recited margin of error, for purposes of identification.

When a molecule or other material is identified herein as "pure", it generally means, unless specified otherwise, that the material is 99% pure or more, as determined by methods conventional in art such as high performance liquid chromatography (HPLC) or optical methods. In general, this refers to purity with regard to unwanted residual solvents, reaction byproducts, impurities, and unreacted starting materials. In the case of stereoisomers, "pure" also means 99% of one enantiomer or diastereomer, as appropriate. "Substantially" pure means, the same as "pure except that the lower limit is about 98% pure or more and likewise, "essentially" pure means the same as "pure" except that the lower limit is about 95% pure.

As used herein, the term "room temperature" refers to a temperature of from about 20° C. to about 35° C., from about 25° C. to about 35° C., from about 25° C. to about 30° C., or for example, about 25° C.

As used herein, the term "overnight" refers to a time interval from about 14 hours to about 24 hours, or about 14 hours to about 20 hours, for example, about 16 hours.

The "polymer" or "carrier" or "excipient" as used herein interchangeably refer to any substance or mixture of substances which are pharmaceutically acceptable inactive ingredients.

The term "dispersed" means random distribution of a therapeutically active substance throughout the carrier.

Certain specific aspects and embodiments of the present application will be explained in greater detail with reference to the following examples, which are provided only for purposes of illustration and should not be construed as limiting the scope of the application in any manner. Reasonable variations of the described procedures are intended to be within the scope of the present invention. While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EXAMPLES

Example 1: Preparation of Amorphous Lumateperone p-Tosylate

Lumateperone p-tosylate (500 mg) was dissolved in methanol (25 mL) at room temperature for clear solution and filtered to remove undissolved particles. The resultant filtrate was subjected to fast solvent evaporation using rotavapor at about 55° C. to afford the solid compound. The said solid was dried under vacuum at about 45° C. to afford the amorphous Lumateperone p-tosylate according to FIG. 1.

Example 2: Preparation of Amorphous Lumateperone p-Tosylate

Lumateperone p-tosylate (500 mg) was dissolved in acetone (80 mL) at room temperature for clear solution and filtered to remove undissolved particles. The resultant filtrate was subjected to fast solvent evaporation using rotavapor at about 55° C. to afford the title compound.

Example 3: Preparation of Amorphous Lumateperone p-Tosylate

Lumateperone p-tosylate (3 g) was dissolved in methanol (150 mL). The solution is filtered to remove undissolved particles and the filtrate was subjected to spray drying at inlet temperature of 70° C. and outlet temperature of −33° C. with a flow rate of 4.9 mL/min to afford the title compound according to FIG. 2.

Example 4: Preparation of Lumateperone p-Tosylate Solid Dispersion with PVPK-30 (1:1 w/w)

Lumateperone p-tosylate (500 mg), PVP K30 (500 mg) were dissolved in methanol (40 mL) at room temperature for clear solution. The mixture was then filtered and filtrate was subjected to solvent evaporation at about 55° C. to afford the title amorphous solid dispersion having X-ray powder diffraction according to FIG. 3.

Example 5: Preparation of Lumateperone p-Tosylate Solid Dispersion with HPC (1:1 w/w)

Lumateperone p-tosylate (500 mg), HPC (500 mg) were dissolved in methanol (55 mL) at room temperature for clear solution. The mixture was then filtered and filtrate was subjected to solvent evaporation at about 55° C. to afford the title amorphous solid dispersion having X-ray powder diffraction according to FIG. 4.

Example 6: Preparation of Lumateperone p-Tosylate Solid Dispersion with HPMC (1:1 w/w)

Figure 5:
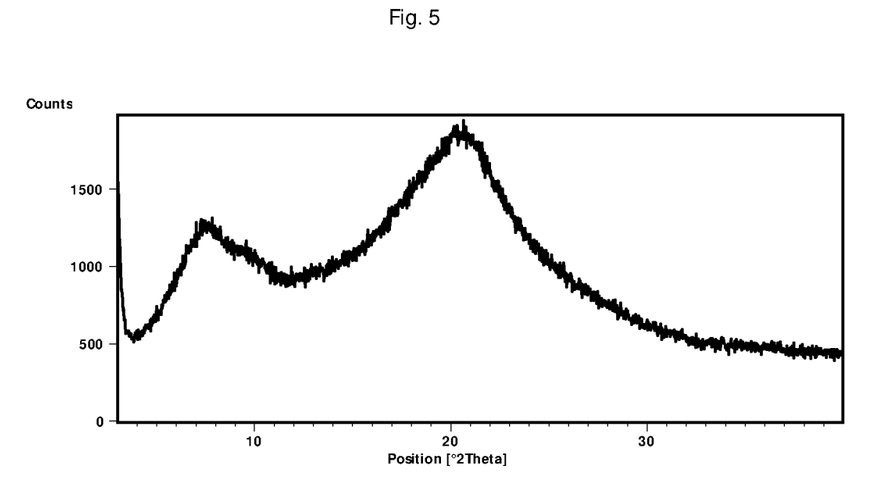
FIG. 5 is an illustration of powder X-ray diffraction ("PXRD") pattern of Lumateperonep-tosylate present in amorphous solid dispersion according to example 6.

Lumateperone p-tosylate (500 mg), HPMC (500 mg) were dissolved in methanol (50 mL) at room temperature for clear solution. The mixture was then filtered and filtrate was subjected to solvent evaporation at about 55° C. to afford the title amorphous solid dispersion having X-ray powder diffraction according to FIG. 5.

Example 7: Preparation of Lumateperone p-Tosylate Solid Dispersion with Syloid 244FP (1:1 w/w)

Lumateperone p-tosylate (200 mg) was dissolved in methanol (30 mL) at room temperature for clear solution followed by filtration to remove undissolved material. To the filtrate, Syloid 244FP (200 mg) was added and the resulting suspension was subjected to fast evaporation at about 55° C. to afford the title amorphous solid dispersion having X-ray powder diffraction according to FIG. 6.

Figure 3:
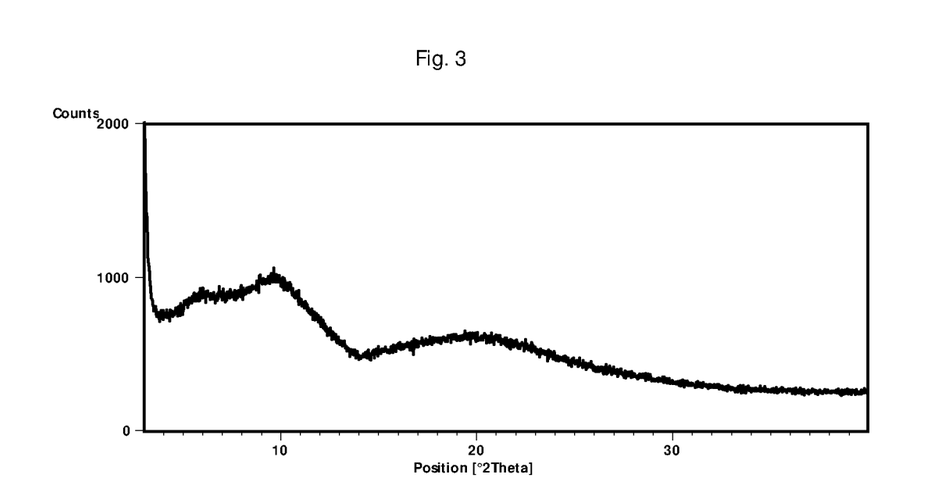
FIG. 3 is an illustration of powder X-ray diffraction ("PXRD") pattern of Lumateperonep-tosylate present in amorphous solid dispersion according to example 4.
Figure 4:
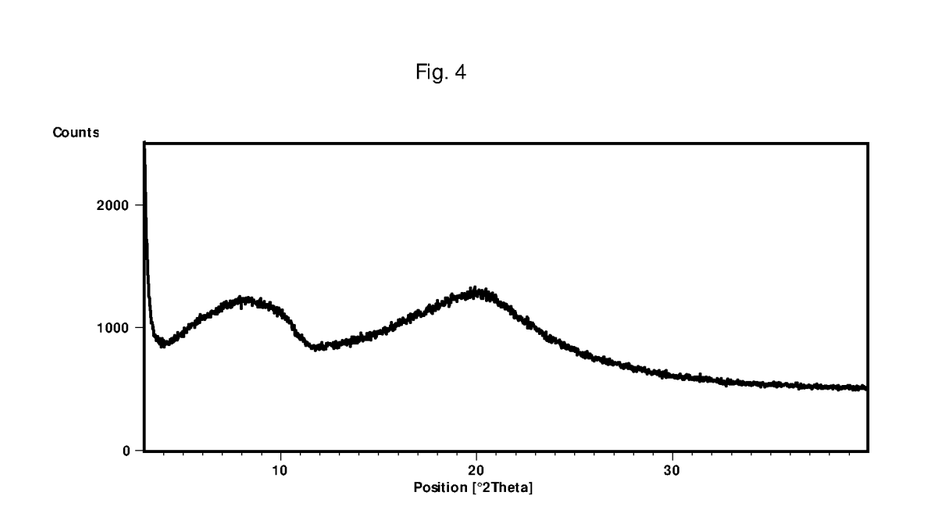
FIG. 4 is an illustration of powder X-ray diffraction ("PXRD") pattern of Lumateperonep-tosylate present in amorphous solid dispersion according to example 5.
Figure 6:
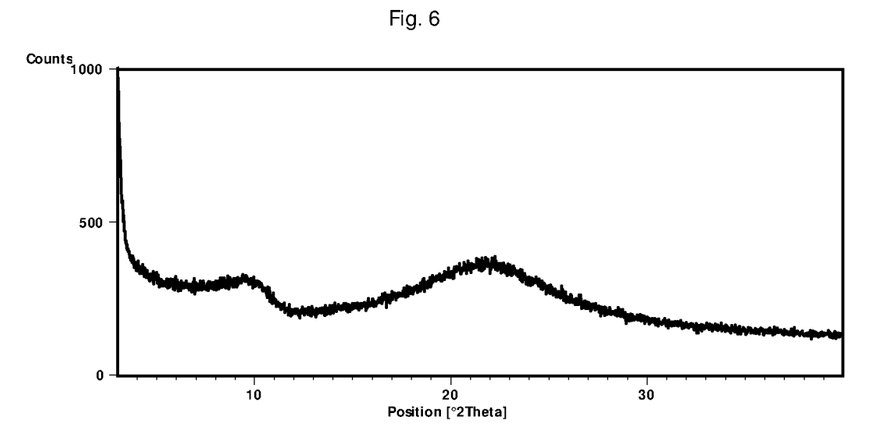
FIG. 6 is an illustration of powder X-ray diffraction ("PXRD") pattern of Lumateperonep-tosylate present in amorphous solid dispersion according to example 7.

The invention claimed is:
1. A solid dispersion comprising amorphous Lumateperone p-tosylate in a dispersing agent;

wherein the amorphous Lumateperone p-tosylate is of the formula:

wherein the amorphous Lumateperone p-tosylate is characterized by a powder X-ray diffraction pattern as illustrated by FIG. 3, FIG. 4, or FIG. 6; and
wherein the dispersing agent is a pharmaceutically acceptable polymer selected from the group consisting of a hydroxypropyl cellulose polymer, a polyvinylpyrrolidone polymer, and a Syloid polymer.

2. The solid dispersion of claim 1, wherein the dispersing agent is a Syloid polymer.

* * * * *